(12) United States Patent
Vidlund et al.

(10) Patent No.: US 11,759,218 B2
(45) Date of Patent: Sep. 19, 2023

(54) MEDICAL SYSTEMS, DEVICES, AND RELATED METHODS

(71) Applicant: J.D. Franco & Co., LLC, Plano, TX (US)

(72) Inventors: Robert Vidlund, Forest Lake, MN (US); Michael Calhoun, Lighthouse Point, FL (US); Jeff Franco, Plano, TX (US)

(73) Assignee: J.D. FRANCO & CO., LLC, Plano, TX (US)

( * ) Notice: Subject to any disclaimer, the term of this patent is extended or adjusted under 35 U.S.C. 154(b) by 558 days.

(21) Appl. No.: 16/938,175

(22) Filed: Jul. 24, 2020

(65) Prior Publication Data

US 2021/0145463 A1  May 20, 2021

Related U.S. Application Data

(63) Continuation of application No. 16/220,413, filed on Dec. 14, 2018, now Pat. No. 10,758,254.

(Continued)

(51) Int. Cl.
*A61M 25/00* (2006.01)
*A61B 17/22* (2006.01)
(Continued)

(52) U.S. Cl.
CPC ......... *A61B 17/22* (2013.01); *A61M 25/0082* (2013.01); *A61M 25/10* (2013.01);
(Continued)

(58) Field of Classification Search
CPC ............ A61B 2217/005; A61M 25/10; A61M 2025/1059; A61M 2025/1052; A61M 2025/1068; A61M 25/0082
See application file for complete search history.

(56) References Cited

U.S. PATENT DOCUMENTS 2,690,595 A   10/1954  Raiche
3,367,101 A   2/1968   Garnet et al.
(Continued)

FOREIGN PATENT DOCUMENTS

EP    2 495 006 A1    9/2012
WO   WO 98/52639 A1   11/1998
(Continued)

OTHER PUBLICATIONS

Altinbas, N.K. et al., "Effect of Carotid Artery Stenting on Ophthalmic Artery Flow Patterns," Journal of Ultrasound Medicine, 2014; 33: pp. 629-638.
(Continued)

*Primary Examiner* — Deanna K Hall
(74) *Attorney, Agent, or Firm* — Bookoff McAndrews, PLLC

(57) ABSTRACT

A method may include delivering a first catheter to a location within an arterial vasculature of a subject. The location may include at least one of an internal carotid artery of the subject or a junction between an ophthalmic artery of the subject and the internal carotid artery of the subject. The method also may include moving a second catheter relative to the first catheter so as to reorient a direction of a distal opening of the second catheter, the second catheter being connected to the first catheter at a joint.

20 Claims, 10 Drawing Sheets

Related U.S. Application Data

(60) Provisional application No. 62/599,155, filed on Dec. 15, 2017.

(51) Int. Cl.
*A61M 25/10* (2013.01)
*A61B 17/00* (2006.01)

(52) U.S. Cl.
CPC .............. *A61B 2017/00323* (2013.01); *A61B 2017/22079* (2013.01); *A61B 2217/005* (2013.01); *A61M 2025/0004* (2013.01)

(56) References Cited

U.S. PATENT DOCUMENTS

| | | | |
|---|---|---|---|
| 3,435,826 A | 4/1969 | Fogarty | |
| 3,970,090 A | 7/1976 | Loiacono | |
| 4,224,929 A | 9/1980 | Furihata | |
| 4,403,612 A | 9/1983 | Fogarty | |
| 4,445,897 A | 5/1984 | Ekbladh et al. | |
| 4,794,931 A | 1/1989 | Yock | |
| 4,857,045 A | 8/1989 | Rydell | |
| 4,886,061 A | 12/1989 | Fischell et al. | |
| 4,894,051 A | 1/1990 | Shiber | |
| 4,898,575 A | 2/1990 | Fischell et al. | |
| 4,926,858 A | 5/1990 | Gifford, III et al. | |
| 4,936,835 A | 6/1990 | Haaga | |
| 4,950,277 A | 8/1990 | Farr | |
| 4,957,482 A | 9/1990 | Shiber | |
| 4,979,939 A | 12/1990 | Shiber | |
| 4,986,807 A | 1/1991 | Farr | |
| 5,000,185 A | 3/1991 | Yock | |
| 5,000,734 A | 3/1991 | Boussignac et al. | |
| 5,007,896 A | 4/1991 | Shiber | |
| 5,019,088 A | 5/1991 | Farr | |
| 5,024,651 A | 6/1991 | Shiber | |
| 5,026,384 A | 6/1991 | Farr et al. | |
| 5,087,265 A | 2/1992 | Summers | |
| 5,100,425 A | 3/1992 | Fischell et al. | |
| 5,135,531 A | 8/1992 | Shiber | |
| 5,176,693 A | 1/1993 | Pannek, Jr. | |
| 5,292,332 A | 3/1994 | Lee | |
| 5,313,949 A | 5/1994 | Yock | |
| 5,314,438 A | 5/1994 | Shturman | |
| 5,318,576 A | 6/1994 | Plassche et al. | |
| 5,336,234 A | 8/1994 | Vigil et al. | |
| 5,366,464 A | 11/1994 | Belknap | |
| 5,395,311 A | 3/1995 | Andrews | |
| 5,402,790 A | 4/1995 | Jang et al. | |
| 5,409,454 A | 4/1995 | Fischell et al. | |
| 5,415,634 A | 5/1995 | Glynn et al. | |
| 5,419,761 A | 5/1995 | Narayanan et al. | |
| 5,507,292 A | 4/1996 | Jang et al. | |
| 5,554,119 A | 9/1996 | Harrison et al. | |
| 5,709,701 A | 1/1998 | Parodi | |
| 5,820,595 A | 10/1998 | Parodi | |
| 5,897,567 A | 4/1999 | Ressemann et al. | |
| 5,951,514 A | 9/1999 | Sahota | |
| 5,972,019 A | 10/1999 | Engelson et al. | |
| 6,010,522 A | 1/2000 | Barbut et al. | |
| 6,146,370 A | 11/2000 | Barbut | |
| 6,206,868 B1 | 3/2001 | Parodi | |
| 6,302,908 B1 | 10/2001 | Parodi | |
| 6,336,933 B1 | 1/2002 | Parodi | |
| 6,344,054 B1 | 2/2002 | Parodi | |
| 6,413,235 B1 | 7/2002 | Parodi | |
| 6,423,032 B2 | 7/2002 | Parodi | |
| 6,494,890 B1 | 12/2002 | Shturman et al. | |
| 6,540,712 B1 | 4/2003 | Parodi et al. | |
| 6,595,980 B1 | 7/2003 | Barbut | |
| 6,623,471 B1 | 9/2003 | Barbut | |
| 6,626,861 B1 | 9/2003 | Hart et al. | |
| 6,641,573 B1 | 11/2003 | Parodi | |
| 6,645,222 B1 | 11/2003 | Parodi et al. | |
| 6,824,558 B2 | 11/2004 | Parodi | |
| 6,827,726 B2 | 12/2004 | Parodi | |
| 6,837,881 B1 | 1/2005 | Barbut | |
| 6,855,162 B2 | 2/2005 | Parodi | |
| 6,902,540 B2 | 6/2005 | Dorros et al. | |
| 6,905,490 B2 | 6/2005 | Parodi | |
| 6,908,474 B2 | 6/2005 | Hogendijk et al. | |
| 6,929,634 B2 | 8/2005 | Dorros et al. | |
| 6,936,053 B1 | 8/2005 | Weiss | |
| 6,936,060 B2 | 8/2005 | Hogendijk et al. | |
| 6,974,469 B2 | 12/2005 | Broome et al. | |
| 7,195,611 B1 | 3/2007 | Simpson et al. | |
| 7,214,201 B2 | 5/2007 | Burmeister et al. | |
| 7,235,095 B2 | 6/2007 | Haverkost et al. | |
| 7,309,334 B2 | 12/2007 | Von Hoffmann | |
| 7,384,411 B1 | 6/2008 | Condado | |
| 7,604,612 B2 | 10/2009 | Ressemann et al. | |
| 7,806,906 B2 | 10/2010 | Don Michael | |
| 7,867,273 B2 | 1/2011 | Pappas et al. | |
| 7,901,445 B2 | 3/2011 | Walker et al. | |
| 7,927,347 B2 | 4/2011 | Hogendijk et al. | |
| 8,123,779 B2 | 2/2012 | Demond et al. | |
| 8,157,760 B2 | 4/2012 | Criado et al. | |
| 8,267,956 B2 | 9/2012 | Salahieh et al. | |
| 8,353,850 B2 | 1/2013 | Ressemann et al. | |
| 8,409,237 B2 | 4/2013 | Galdonik et al. | |
| 8,414,516 B2 | 4/2013 | Chang | |
| 8,439,937 B2 | 5/2013 | Montague et al. | |
| 8,545,432 B2 | 10/2013 | Renati et al. | |
| 8,834,404 B2 | 9/2014 | Beaudin | |
| 8,852,226 B2 | 10/2014 | Gilson et al. | |
| 8,863,631 B1 | 10/2014 | Janardhan et al. | |
| 9,078,682 B2 | 7/2015 | Lenker et al. | |
| 9,241,699 B1 | 1/2016 | Kume et al. | |
| 9,259,215 B2 | 2/2016 | Chou et al. | |
| 9,265,512 B2 | 2/2016 | Garrison et al. | |
| 9,987,164 B2 | 6/2018 | Calhoun | |
| 10,195,077 B2 | 2/2019 | Calhoun et al. | |
| 10,265,085 B2 | 4/2019 | Zaidat | |
| 10,342,699 B2 | 7/2019 | Calhoun et al. | |
| 2001/0001114 A1 | 5/2001 | Tsugita et al. | |
| 2002/0038103 A1 | 3/2002 | Estrada et al. | |
| 2002/0077656 A1 | 6/2002 | Ginn et al. | |
| 2002/0077658 A1 | 6/2002 | Ginn | |
| 2002/0087128 A1 | 7/2002 | Paques et al. | |
| 2002/0143291 A1 | 10/2002 | Slater | |
| 2002/0151922 A1 | 10/2002 | Hogendijk et al. | |
| 2002/0165573 A1 | 11/2002 | Barbut | |
| 2003/0023200 A1 | 1/2003 | Barbut et al. | |
| 2003/0023227 A1 | 1/2003 | Zadno-Azizi et al. | |
| 2003/0199802 A1 | 10/2003 | Barbut | |
| 2003/0199819 A1 | 10/2003 | Beck | |
| 2003/0203958 A1 | 10/2003 | Kunz et al. | |
| 2005/0149117 A1 | 7/2005 | Khosravi et al. | |
| 2006/0089618 A1 | 4/2006 | McFerran et al. | |
| 2006/0136022 A1 | 6/2006 | Wong, Jr. et al. | |
| 2006/0259132 A1 | 11/2006 | Schaffer et al. | |
| 2006/0276838 A1 | 12/2006 | Wensel et al. | |
| 2007/0026035 A1 | 2/2007 | Burke et al. | |
| 2008/0027519 A1 | 1/2008 | Guerrero | |
| 2008/0243229 A1 | 10/2008 | Wallace et al. | |
| 2009/0018455 A1 | 1/2009 | Chang | |
| 2009/0024072 A1 | 1/2009 | Criado et al. | |
| 2009/0030323 A1 | 1/2009 | Fawzi et al. | |
| 2009/0221961 A1 | 9/2009 | Tal et al. | |
| 2010/0076365 A1 | 3/2010 | Riina et al. | |
| 2010/0100045 A1 | 4/2010 | Pravongviengkham et al. | |
| 2010/0125244 A1 | 5/2010 | McAndrew | |
| 2010/0234884 A1 | 9/2010 | Lafontaine et al. | |
| 2011/0143993 A1 | 6/2011 | Langer et al. | |
| 2011/0152683 A1 | 6/2011 | Gerrans et al. | |
| 2011/0152998 A1 | 6/2011 | Berez et al. | |
| 2011/0160762 A1 | 6/2011 | Hogendijk et al. | |
| 2011/0274748 A1 | 11/2011 | Robinson et al. | |
| 2012/0046679 A1 | 2/2012 | Patel et al. | |
| 2012/0078287 A1 | 3/2012 | Barbut | |
| 2012/0101510 A1 | 4/2012 | Lenker et al. | |
| 2013/0035628 A1 | 2/2013 | Garrison et al. | |
| 2013/0197621 A1 | 8/2013 | Ryan et al. | |
| 2013/0281788 A1 | 10/2013 | Garrison | |

(56) References Cited

U.S. PATENT DOCUMENTS

| | | | |
|---|---|---|---|
| 2014/0154246 A1 | 6/2014 | Robinson et al. |
| 2014/0222066 A1 | 8/2014 | Tegels |
| 2015/0025562 A1 | 1/2015 | Dinh et al. |
| 2015/0032121 A1 | 1/2015 | Janardhan et al. |
| 2015/0065804 A1 | 3/2015 | Kleyman |
| 2015/0231378 A1 | 8/2015 | Pepper |
| 2015/0272732 A1 | 10/2015 | Tilson et al. |
| 2015/0313607 A1 | 11/2015 | Zhadkevich |
| 2015/0359547 A1 | 12/2015 | Vale et al. |
| 2015/0359549 A1 | 12/2015 | Lenker et al. |
| 2015/0366580 A1 | 12/2015 | Lenihan et al. |
| 2016/0166754 A1 | 6/2016 | Kassab et al. |
| 2016/0317328 A1 | 11/2016 | Berez et al. |
| 2017/0164963 A1 | 6/2017 | Goyal |
| 2017/0239453 A1 | 8/2017 | Kawakita et al. |
| 2017/0326001 A1 | 11/2017 | Franco et al. |
| 2017/0348120 A1 | 12/2017 | Calhoun et al. |
| 2018/0132876 A1 | 5/2018 | Zaidat |

FOREIGN PATENT DOCUMENTS

| | | | |
|---|---|---|---|
| WO | WO 98/53761 A1 | 12/1998 |
| WO | WO 00/54673 A1 | 9/2000 |
| WO | WO 03/018085 A2 | 3/2003 |
| WO | WO 2007/103464 A2 | 9/2007 |
| WO | WO 2011/156782 A1 | 12/2011 |
| WO | WO 2012/162651 A1 | 11/2012 |
| WO | WO 2014/022866 A1 | 2/2014 |
| WO | WO 2016/109586 A1 | 7/2016 |
| WO | WO 2016/149653 A2 | 9/2016 |
| WO | WO 2017/156333 A1 | 9/2017 |
| WO | WO 2018/053121 A1 | 3/2018 |
| WO | WO 2018/106858 A1 | 6/2018 |

OTHER PUBLICATIONS

Ambarki, K. et al., "Blood Flow of Ophthalmic Artery in Healthy Individuals Determined by Phase-Contrast Magnetic Resonance Imaging," Investigative Ophthalmology & Visual Science, 2013; 54: pp. 2738-2745.

Hayreh, S.S., "The Ophthalmic Artery III. Branches," British Journal of Ophthalmology, 1962, 46, pp. 212-247.

Hwang, G. et al., "Reversal of Ischemic Retinopathy Following Balloon Angioplasty of a Stenotic Ophthalmic Artery." Journal of Neuro-Ophthalmology 30.3, 2010, pp. 228-230.

Kane, A.G. et al., "Reduced Caliber of the Internal Carotid Artery: A Normal Finding with Ipsilateral Absence or Hypoplasia of the A1 Segment," American Journal of Neuroradiology, 1996; 17: pp. 1295-1301.

Kawa, M.P. et al., "Complement System in Pathogenesis of AMD: Dual Player in Degeneration and Protection of Retinal Tissue," Hindawi Publishing Corporation, Journal of Immunology Research, vol. 2014, Article ID 483960, 12 pages.

Klein, R. et al., "Vasodilators, Blood Pressure-Lowering Medications, and Age-Related Macular Degeneration," American Academy of Ophthalmology, 2014, vol. 121, Issue 8, pp. 1604-1611.

Kooragayala, K. et al., "Quanitification of Oxygen Consumption in Retina Ex Vivo Demonstrates Limited Reserve Capacity of Photoreceptor Mitochondria," Investigative Ophthalmology & Visual Science, 2015; 56: pp. 8428-8436.

Krejza, J. et al., "Carotid Artery Diameter in Men and Women and the Relation to Body and Neck Size," Stroke, 2006; 3 pages.

Lanzino, G. et al., "Treatment of Carotid Artery Stenosis: Medical Therapy, Surgery, or Stenting?," Mayo Clinic Proceedings, Apr. 2009; 84(4), pp. 362-368.

Michalinos, A. et al., "Anatomy of the Ophthalmic Artery: A Review concerning Its Modern Surgical and Clinical Applications," Hindawi Publishing Corporation, Anatomy Research International, vol. 2015, Article ID 591961, 8 pages.

Paques, M. et al., "Superselective ophthalmic artery fibrinolytic therapy for the treatment of central retinal vein occlusion." British Journal of Ophthalmology, 2000, 84: 1387-1391.

Tan, P.L. et al., "AMD and the alternative complement pathway: genetics and functional implications," Human Genomics, 2016, 10:23, 13 pages.

Xu, H. et al., "Targeting the complement system for the management of retinal inflammatory and degenerative diseases," European Journal of Pharmacology, 2016, 787, pp. 94-104.

Yamane, T. et al., "The technique of ophthalmic arterial infusion therapy for patients with intraocular retinoblastoma," International Journal of Clinical Oncology, Apr. 2004; vol. 9, Issue 2, pp. 69-73.

Zeumer, H. et al., "Local intra-arterial fibrinolytic therapy in patients with stroke: urokinase versus recombinant tissue plagminogen activator (r-TPA)," Neuroradiology, 1993; 35: pp. 159-162.

Zipfel, P.F., et al., "The Role of Complement in AMD," Inflammation and Retinal Disease: Complement Biology and Pathology, Advances in Experimental Medicine and Biology, 2010, 703, pp. 9-24.

Examination Report No. 2 for AU Application No. 2013296195, dated Jun. 27, 2017 (6 pages).

Notice of Allowance for KR 20157005602, dated Sep. 25, 2017 (3 pages).

Loh, K. et al., "Prevention and management of vision loss relating to facial filler injections." Singapore Medical Journal, 2016; 57(8): 438-443.

International Search Report and Written Opinion for International Application No. PCT/US2017/051551, dated Dec. 15, 2017 (14 pages).

International Search Report and Written Opinion for International Application No. PCT/US2017/052901, dated Dec. 8, 2017 (9 pages).

Hayreh et al., "Ocular Arterial Occlusive Disorders and Carotid Artery Disease," American Academy of Ophthalmology, 2017; vol. 1, No. 1: pp. 12-18.

Hayreh et al., "The Ophthalmic Artery," Brit. J. Ophthal., 1962; 46, 65: pp. 65-98.

Bird, B. et al., "Anatomy, Head and Neck, Ophthalmic Arteries," NCBI Bookshelf, a service of the National Library of Medicine, National Institutes of Health, Oct. 27, 2018, 5 pages. www.ncbi.nlm.nih.gov/books/NBK482317/.

Hattenbach, L. et al., "Experimental Endoscopic Endovascular Cannulation: A Novel Approach to Thrombolysis in Retinal Vessel Occlusion," Investigative Ophthalmology & Visual Science, Jan. 2012, vol. 53, No. 1, pp. 42-46.

Khan, T.T. et al., "An Anatomical Analysis of the Supratrochlear Artery: Considerations in Facial Filler Injections and Preventing Vision Loss," Aesthetic Surgery Journal, 2017, vol. 37(2), pp. 203-208.

Schumacher, M. et al., "Intra-arterial fibrinolytic therapy in central retinal artery occlusion," Neuroradiology (1993) 35: pp. 600-605.

Schwenn, O.K. et al., "Experimental Percutaneous Cannulation of the Supraorbital Arteries: Implication for Future Therapy," Investigative Ophthalmology & Visual Science, May 2005, vol. 46, No. 5, pp. 1557-1560.

Wang, R. et al., "Evaluation of Ophthalmic Artery Branch Retrograde Intervention in the Treatment of Central Retinal Artery Occlusion (CRAO)," Medical Science Monitor, 2017, 23: pp. 114-120.

Zhao, W. et al. "Three-Dimensional Computed Tomographic Study on the Periorbital Branches of the Ophthalmic Artery: Arterial Variations and Clinical Relevance," Aesthetic Surgery Journal, 2018, pp. 1-9.

International Search Report and Written Opinion for corresponding PCT/US2013/053670, dated Dec. 26, 2013 (16 pp.).

International Search Report and Written Opinion for International Application No. PCT/US2018/031229, dated Jul. 27, 2018 (19 pages).

Mazur et al., Catheterization and Cardiovascular Diagnosis, vol. 31, Issue 1, Abstract (1994).

(56) References Cited

OTHER PUBLICATIONS

Aurboonyawat et al., "Indirect Carotid-Cavernous Sinus Fistulas Treated by Transvenous Approach Through the Superior Ophthalmic Vein: A Case Report and Technical Note," Siriraj Med. J., vol. 59, pp. 191-194, 2007.
Kleintjes, "Forehead anatomy: Arterial variations and venous link of the midline forehead flap," Journal of Plastic, Reconstructive & Aesthetic Surgery, vol. 60, Issue 6, pp. 593-606, 2007.
International Search Report and Written Opinion for International Application No. PCT/US2018/014766, dated Mar. 29, 2018 (7 pages).
International Search Report and Written Opinion for International Application No. PCT/US2019/068758, dated May 29, 2020 (16 pages).
Extended European Search Report for EP 18745369.1, dated Nov. 18, 2020 (6 pages).

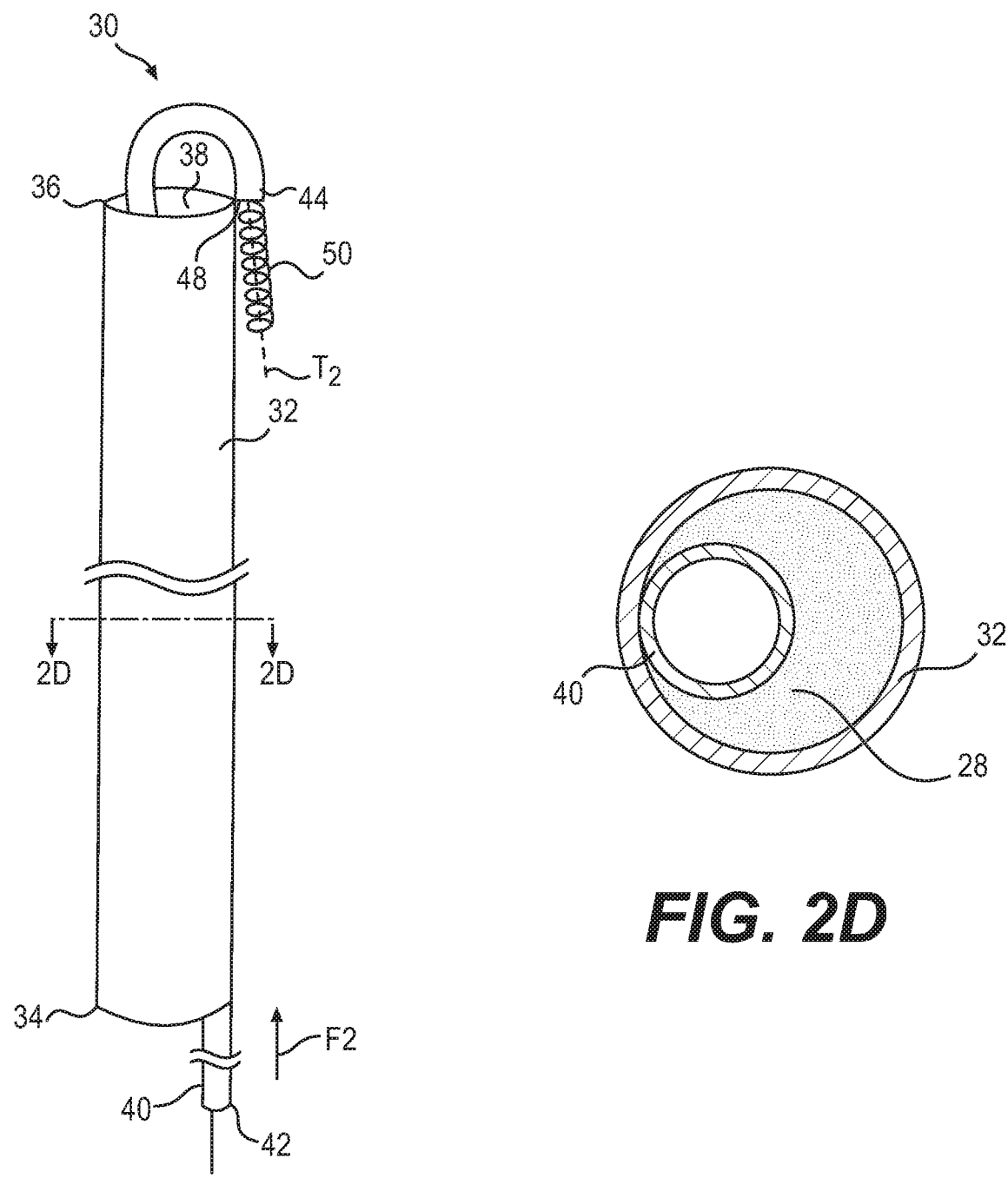

MEDICAL SYSTEMS, DEVICES, AND RELATED METHODS

CROSS-REFERENCE TO RELATED APPLICATIONS

This patent application claims the benefit of priority under 35 U.S.C. § 119 to U.S. Provisional Patent Application No. 62/599,155, filed Dec. 15, 2017, which is herein incorporated by reference in its entirety.

TECHNICAL FIELD

Various aspects of the present disclosure relate generally to medical systems, devices, and related methods. More specifically, the present disclosure relates to medical systems and/or devices for delivery of one or more devices and/or tools to or within the ophthalmic artery.

BACKGROUND

Vasculature of a subject (also referred to as a patient) may occasionally become stenosed, occluded, partially occluded, blocked, narrowed, or otherwise compromised such that transfer of blood through the vasculature is impeded, lessened, and/or prevented. That is, the blood carrying capacity of such a compromised vessel is reduced or otherwise insufficient. The vasculature may become occluded, stenosed, or at least partially blocked due to the deposit of plaque, emboli, or other such material on the walls of the vasculature. To avoid serious and/or permanent injury, one or more medical procedures or interventions may be performed. Such procedures may include, for example, angioplasty, atherectomy, stenting, or the like, in which a constricted, narrowed, occluded, fully blocked, or partially blocked region of the vasculature is opened, widened, or unblocked so as to allow or maintain blood flow therethrough. Often, however, such procedures are impractical or impossible in the tortuous and small-scale vasculature supporting an eye of a patient.

The systems, devices, and methods of the current disclosure may rectify some of the deficiencies described above or address other aspects of the prior art.

SUMMARY

Examples of the present disclosure relate to, among other things, medical devices and procedures. Each of the examples disclosed herein may include one or more of the features described in connection with any of the other disclosed examples.

In one example, a method may include delivering a first catheter to a location within an arterial vasculature of a subject. The location may include at least one of an internal carotid artery of the subject or a junction between an ophthalmic artery of the subject and the internal carotid artery of the subject. The method also may include moving a second catheter relative to the first catheter so as to reorient a direction of a distal opening of the second catheter, the second catheter being connected to the first catheter at a joint.

Examples of the method may include one or more of the following features. The moving the second catheter may include bending the second catheter. The method may further include adjusting a degree of bending of the second catheter. The method may further include directing a guide wire through the distal opening of the second catheter and into the ophthalmic artery. The method may further include securing the second catheter relative to the first catheter via a balloon. The method may further include applying aspiration to the location via the second catheter. The joint may include a hinge.

In a further example, a method may include delivering a first catheter to a location within an internal carotid artery of a subject. Additionally, the method may include manipulating a second catheter at least partially received within the first catheter. The manipulating may include adjusting an angle of a distal opening of the second catheter relative to an axis of the first catheter. Further, the method may include securing a position of the second catheter relative to the first catheter.

Examples of the method may include any one or more of the following features. Adjusting the angle may include positioning the distal opening to face an ophthalmic artery of the subject. The method may further include advancing the distal opening of the second catheter through a side port of the first catheter, and the side port may extend through a side wall of the first catheter between a proximal end of the first catheter and a distal end of the first catheter. The method may further include adjusting a degree of expansion of an expandable member associated with the side port. The manipulating the second catheter may include steering the second catheter to form a first bend, the first bend being approximately 90° or approximately 180°. Additionally, where the first bend is approximately 180°, the manipulating the second catheter may further include steering the second catheter to form a second bend, the second bend being approximately 90°. The method may further include applying aspiration via the second catheter.

In a further example, a method may include advancing a first catheter to a location within an internal carotid artery of a subject. Additionally, the method may include bending a second catheter relative to the first catheter so as to adjust an angle of a distal opening of the second catheter relative to an axis of the first catheter and advancing a guidewire through the second catheter, beyond the distal opening, and into an ophthalmic artery of the subject.

Examples of the method may include any one or more of the following features. The bending the second catheter may include steering the second catheter to form a first bend, the first bend being approximately 90° or approximately 180°. The bending the second catheter may include positioning the distal opening to face the ophthalmic artery. The method may further include securing the second catheter to the first catheter via an expandable element. The method may further include adjusting an expansion degree of the expandable element. The method may further include applying aspiration via the second catheter.

Both the foregoing general description and the following detailed description are exemplary and explanatory only and are not restrictive of the features of the inventive devices and methods. As used herein, the terms "comprises," "comprising," "having," "including," or other variations thereof, are intended to cover a non-exclusive inclusion such that a process, method, article, or apparatus that comprises a list of elements does not necessarily include only those elements, but may include other elements not expressly listed or inherent to such a process, method, article, or apparatus. Additionally, the term "exemplary" is used herein in the sense of "example," rather than "ideal." As used herein, the terms "about," "substantially," and "approximately," indicate a range of values within +/−10% of the stated value unless otherwise stated.

BRIEF DESCRIPTION OF THE DRAWINGS

The accompanying drawings, which are incorporated in and constitute a part of this specification, illustrate exemplary features of the present disclosure and together with the description, serve to explain the principles of the disclosure.

FIGS. 2A-2C illustrate an exemplary system for accessing the OA;

FIG. 2D illustrates a cross-sectional view of FIG. 2C taken along line 2D-2D;

DETAILED DESCRIPTION

Examples of the present disclosure relate to medical systems, devices, and methods for treating internal areas of a patient's body by permitting access to the ophthalmic artery.

Reference will now be made in detail to examples of the present disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary medical device or insertion device. When used herein, "proximal" refers to a position relatively closer to the exterior of the body or closer to a medical professional using the medical device or insertion device. In contrast, "distal" refers to a position relatively further away from the medical professional using the medical device or insertion device, or closer to the interior of the body.

The terms "downstream" or "antegrade" and "upstream" or "retrograde," when used herein in relation to the subject's vasculature, refer respectively, to the direction of blood flow and the direction opposite that of blood flow, respectively. In the arterial system, "downstream" or "antegrade" refers to the direction further from the heart, while "upstream" or "retrograde" refers to the direction closer to the heart.

"Reverse flow," as used herein, is the flow of blood opposite to the direction of blood flow under normal blood flow conditions. In this disclosure, "reverse flow" and "retrograde flow" are used synonymously. Reverse flow may be achieved by creating a pressure gradient so blood flow is reversed and directed, for example, from the treatment site into a lumen of a medical device to be rerouted to another location.

Figure 1:
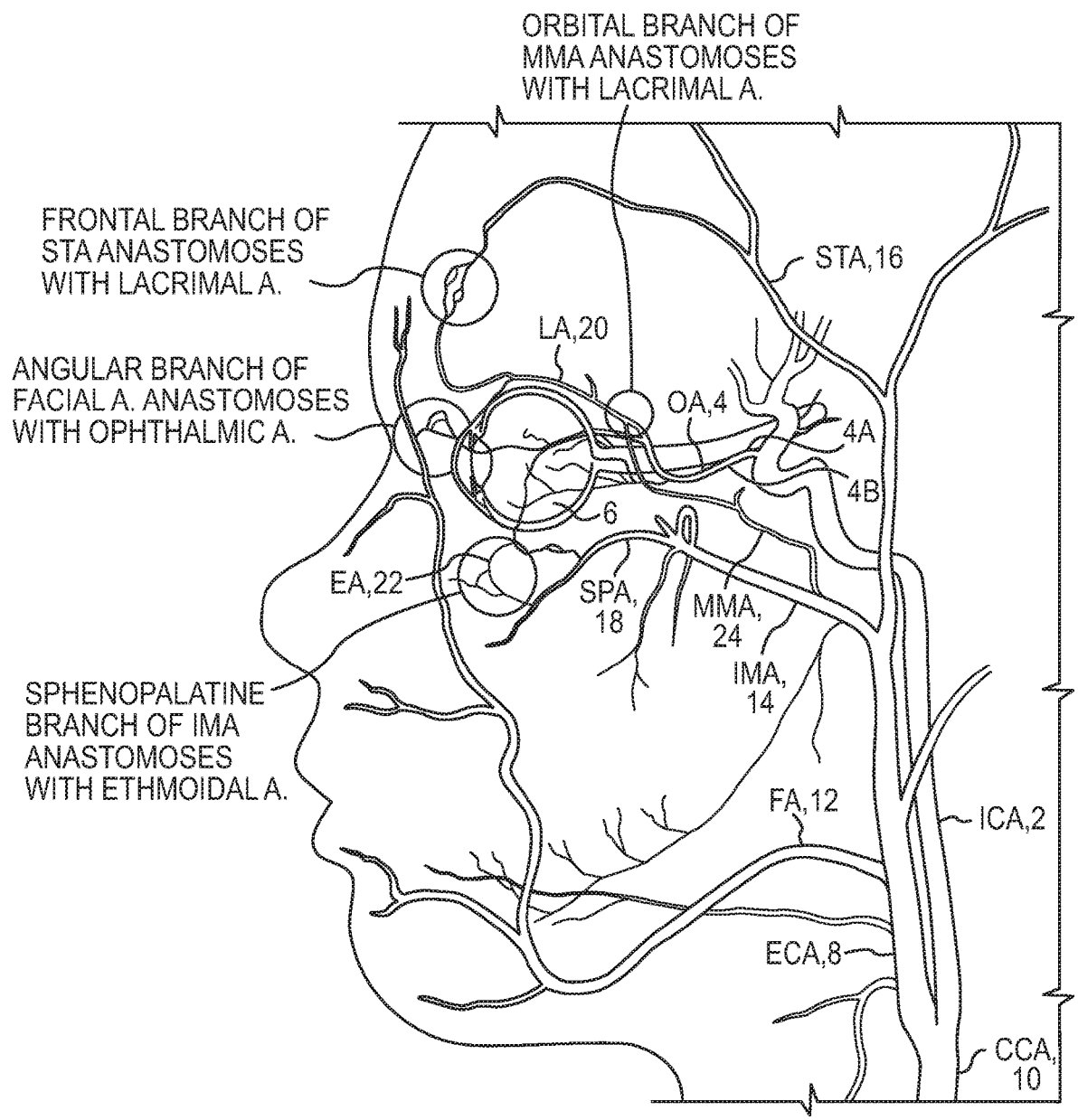
FIG. 1 illustrates vasculature relating to an ophthalmic artery (OA) of a subject.

FIG. 1 illustrates various vasculature structures of a subject. For example, blood may flow from the heart through the internal carotid artery (ICA) 2 to the ophthalmic artery (OA) 4, including a short limb 4A and a long limb 4B, to an eye 6 of the subject. Additionally, the external carotid artery (ECA) 8 may supply a flow of blood to the face and neck of a subject. Each of the ICA 2 and ECA 8 branches off of the common carotid artery (CCA) 10 of the subject. The ECA 8, in turn, branches into the facial artery (FA) 12, the internal maxillary artery (IMA) 14, and the supra trochlear artery (STA) 16. IMA 14 then branches into the sphenopalatine artery (SPA) 18, and the middle meningeal artery (MMA) 24. OA 4 includes a number of branches such as the lacrimal artery (LA) 20 and the ethmoidal artery (EA) 22.

Current procedures, techniques, and devices for the treatment of stenosed, occluded, partially occluded, blocked, narrowed, or otherwise compromised vasculature may be insufficient to permit access to treat a compromised OA 4. Indeed, as shown in FIG. 1, OA 4 (e.g., short limb 4A of OA 4) extends at an angle of about 90° relative to ICA 2. In some subjects, however, this angle is even more extreme such that the OA 4 (e.g., short limb 4A of OA 4) extends at an acute angle relative to ICA 2. Additionally, as shown in FIG. 1, long limb 4B extends at an angle relative to short limb 4A. Such sharp bends or otherwise tortuous transitions between ICA 2 and OA 4 present significant challenges to medical professionals in their efforts to treat, access, insert, and/or deliver one or more devices or substances to locations within the OA 4. Further complicating such procedures, the average OA 4 has a diameter between about 0.7 mm and about 1.8 mm, or generally about 1.2 mm, while the ICA 2 has a diameter between about 3.88 mm and about 5.44 mm, or generally about 4.66 mm in women, and between about 4.24 mm and about 5.98 mm, or generally about 5.11 mm in men. This sharp, abrupt, and/or marked decrease in size affects blood flow characteristics between the ICA 2 and OA 4, and limits the size of devices that may be delivered into or received within the OA 4. Such diameter differences between the OA 4 and the ICA 2, and the takeoff angle of the OA 4 from the ICA 2 (e.g., about 90°) makes device navigation into the OA 4 very difficult.

Figure 2A:
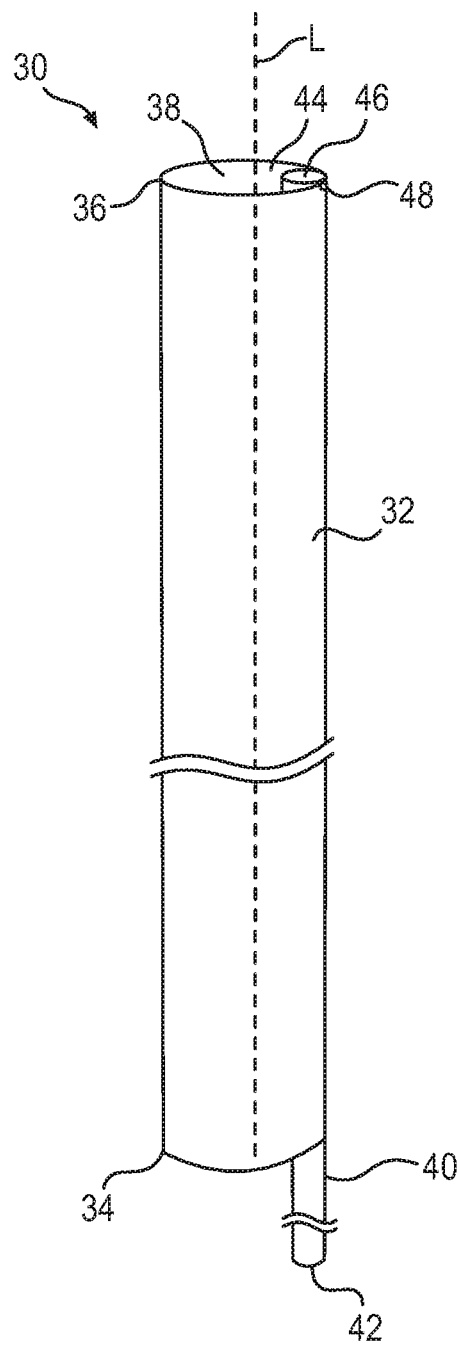
Figure 2B:
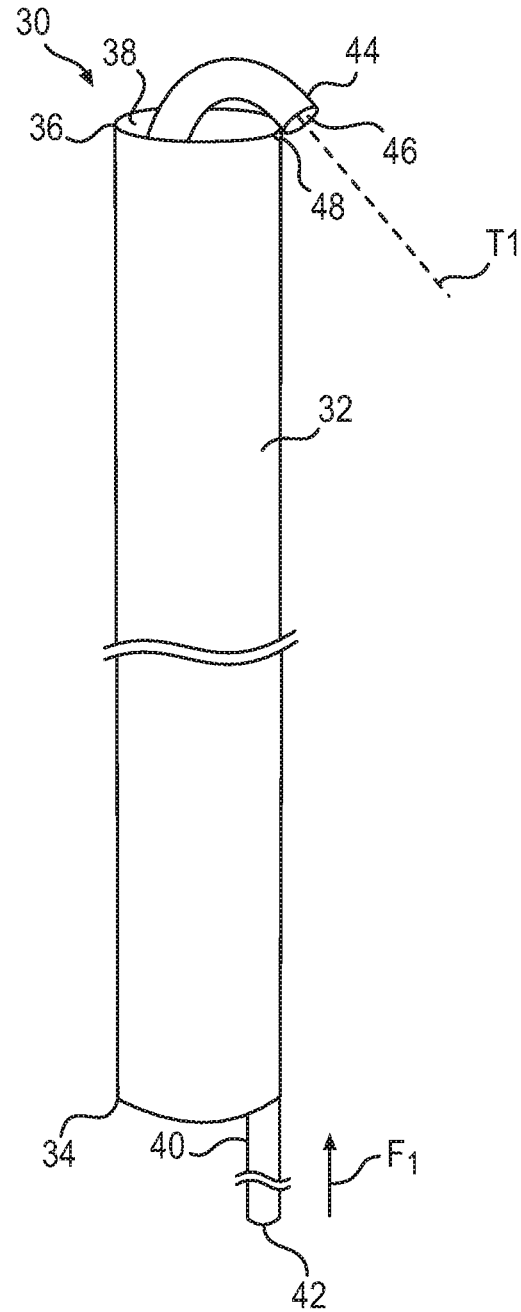

FIGS. 2A-2C illustrate an exemplary system 30 for accessing the OA 4. Such a system may include a guide catheter 32 having a longitudinal axis L, a proximal end 34, a distal end 36, and a lumen 38 extending therebetween. Guide catheter 32 may be employed by a medical professional to establish a pathway to selected anatomy within a patient. That is, distal end 36 of guide catheter 32 is typically inserted into the femoral artery in the thigh area and maneuvered (e.g., steered via any appropriate manner such as steering wires/cables, or tracked over a guidewire, etc.) through the vascular system until the distal end 36 is advanced into the ICA 2, toward the OA 4. The proximal end 34 of the guide catheter 32 may remain outside of the patient providing an access point to the guide catheter lumen 38. An intermediate catheter 40 is at least partially received within lumen 38 of guide catheter 32. As shown in FIGS. 2A-2C, a cross-sectional dimension (e.g., diameter) of intermediate catheter 40 is smaller than a cross-sectional dimension (e.g., diameter) of guide catheter 32. For example, guide catheter 32 may have a cross-sectional dimension of between about 5 FR and about 6 FR, while intermediate catheter 40 may have a cross-sectional dimension between about 3 FR and about 4 FR. Stated differently, intermediate catheter 40 may have a cross-sectional dimension that is between about 60-70% of the cross-sectional dimension of guide catheter 32. Intermediate catheter 40 includes a proximal end 42, a distal end 44, and a lumen 46 extending therebetween.

Figure 2E:
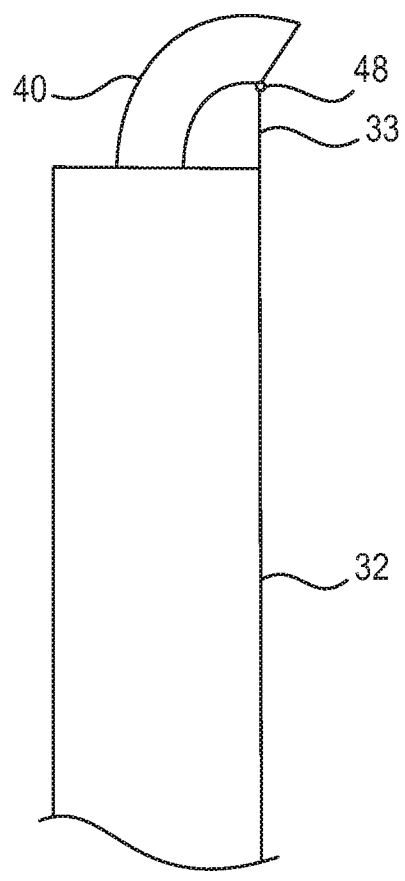
FIGS. 2E and 2F illustrate further exemplary features of the system of FIGS. 2A-2C.
Figure 2F:
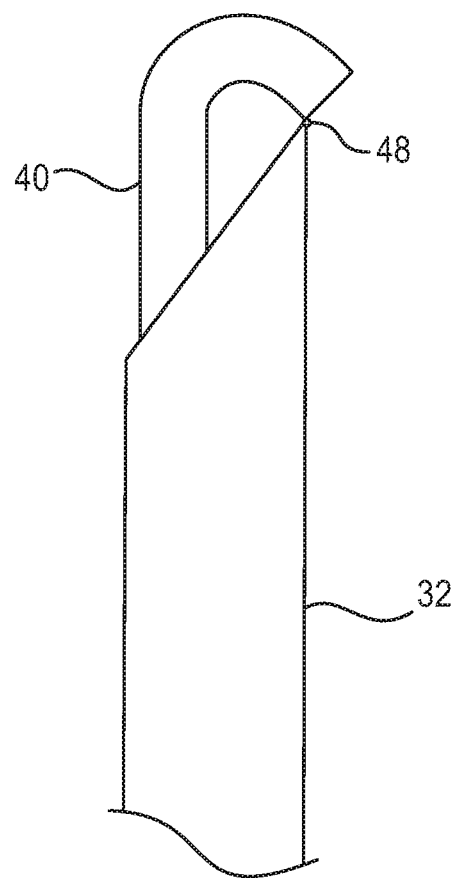

Intermediate catheter 40 may be attached to guide catheter 32 via at least one hinge, flexure point, articulation point, link, and/or joint 48. As shown, joint 48 may be disposed between distal end 44 of intermediate catheter 40 and distal end 36 of guide catheter 32. Joint 48 may be the only point of fixed connection between guide catheter 32 and intermediate catheter 40. That is, a remainder of intermediate catheter 40 is moveable (e.g., axially translatable) relative to guide catheter 32, as shown in FIGS. 2A-2C. For example, a force F may be applied in any appropriate manner (e.g., pushing or pulling) to one or more portions of intermediate catheter 40 so as to displace intermediate catheter 40 relative to guide catheter 32. Additionally, due to joint 48, displacement (e.g., advancement) of intermediate catheter 40 may result in a bending, angling, or curving of intermediate catheter 40 so as to adjust a trajectory or direction of intermediate catheter 40. As shown in FIGS. 2B and 2C, the degree of bending of intermediate catheter 40 is adjustable. For example, as shown in FIG. 2B, upon application of a force F1 having a first magnitude in the direction of distal ends 36 and 44, a distal region of intermediate catheter 40 may bend to a first degree so as to orient distal end 44 of intermediate catheter 40 along a first trajectory T1. Additionally, as shown in FIG. 2C, upon application of a force F2 having a second magnitude greater than the first magnitude in the direction of distal ends 36 and 44, a distal region of intermediate catheter 40 may bend to a second degree so as to orient distal end 44 of intermediate catheter 40 along a second trajectory T2. As shown, the second trajectory of intermediate catheter 40 is sharper or angled along an axis closer to parallel with longitudinal axis L of guide catheter 32. While trajectories T1 and T2 are shown in FIGS. 2B and 2C, respectively, it is understood that such positions or relative angles are merely exemplary and should not be considered descriptive of the only, or the minimum and maximum angles of trajectory of intermediate catheter 40. Rather, upon the application of any force F in a direction towards distal ends 36 and 44, the trajectory of intermediate catheter 40 may be adjusted. Such a trajectory of intermediate catheter 40 may be directly proportional to the magnitude of force F applied. In some arrangements, upon the application of a sufficient force, the trajectory of intermediate catheter 40 may be generally parallel with longitudinal axis L. It is understood that intermediate catheter 40, or at least a distal portion thereof, is sufficiently flexible to permit or enable intermediate catheter 40 to attain the trajectories T1 and T2 shown in FIGS. 2B and 2C. For example, in some arrangements, intermediate catheter 40 may comprise a plurality of discrete articulable links, or may be comprised of a sufficiently flexible material so as to deflect or bend as shown in FIGS. 2B and 2C. Optionally, as shown in FIG. 2E, joint 48 may be located on an extension or arm 33 extending (e.g., extending distally along an axis parallel with a central longitudinal axis of guide catheter 32) from a distal end of guide catheter 32. Arm 33 may be a distal portion of a wire or cable that extends within guide catheter 32, and in certain embodiments, within a separate lumen within guide catheter 32, to a proximal end proximate a user. The user then can extend retract arm 33 to position intermediate catheter 40. In other arrangements, arm 33 may extend along an axis transverse with respect to the central longitudinal axis of guide catheter 32. In still other embodiments, arm 33 may extend along an axis collinear with the central longitudinal axis of guide catheter 32. Additionally, guide catheter 32 may optionally include a beveled or angled tip, as shown in FIG. 2F, without departing from the scope of the disclosure. Further, intermediate catheter 40 may include any one or more of an imaging lumen for delivering one or more imaging elements (e.g., optical fibers, cameras, etc.), one or more radiopaque elements, and/or visual indicators such that a trajectory or angle of intermediate catheter 40 may be readily determined (e.g., via an imaging element and/or via one or more imaging modalities such as fluoroscopy).

In use, guide catheter 32 may be delivered through the vasculature such that distal end 36 is positioned at a desired location, e.g., within the ICA 2 and adjacent or near OA 4. As intermediate catheter 40 is coupled to guide catheter 32 at joint 48, delivery of guide catheter 32 results in likewise delivery of intermediate catheter 40 within the vasculature of a subject. Next, a force F (e.g., F1, F2, any magnitude of force between F1 and F2, a force less than F1, or a force greater than F2) may be applied to intermediate catheter 40 so as to adjust a trajectory of intermediate catheter 40, as desired. Once the trajectory of intermediate catheter 40 has been modified or manipulated as desired, the medical professional may deliver one or more additional medical devices/tools 50 (e.g., a guidewire such as a platinum coiled guidewire, a balloon, etc.) through lumen 46 of intermediate catheter 40 and to a desired location of the anatomy (e.g., within the OA 4). Additionally or alternatively, lumen 46 of intermediate catheter 40 may be coupled to a source of negative pressure (e.g., vacuum, aspiration, suction, etc.) for facilitating retrograde blood flow of OA 4 therethrough. Still further, lumen 46 of intermediate catheter 40 may be used to deliver (e.g., inject) one or more pharmaceuticals or other fluids therethrough. For example, Sildenafil (or an equivalent PDE5 inhibitor), Lucentis, Avastin, Taxol, Rapamyacin, and/or other pharmaceuticals used to improve vascular blood flow may be delivered via lumen 46 of intermediate catheter 40. In addition, pharmaceuticals used to treat re-perfusion injury, such as adenosine, may be also be delivered via lumen 46 of intermediate catheter 40.

Guide catheter 32 and intermediate catheter 40 may be comprised of any appropriate materials such as, for example, silicon, vinyl, polyurethane, polyethylene, Teflon, PTFE, ePTFE, nylon, combinations thereof, or any other suitable biocompatible materials. In some arrangements, intermediate catheter 40 may be more flexible than guide catheter 32. Additionally, joint 48 may be comprised of any appropriate materials such as a shape memory alloy (e.g., Nitinol), biocompatible fibers, and/or polymers. In the case of a shape memory alloy, application of a force F on intermediate catheter 40 may not be necessary. Rather, after the introduction of system 30 within the vasculature of a subject, intermediate catheter 40 may return to a "remembered" or previously established shape (e.g., the bent or curved shape of either FIG. 2B or 2C) due to the properties of the shape memory joint 48. That is, during insertion of intermediate catheter 40 into the subject, a force is applied to intermediate catheter 40 to retain a distal portion of intermediate catheter 40 in a substantially straight configuration within lumen 38 of guide catheter 32. Upon desired positioning within the ICA 2, that force may be lessened or removed, allowing the distal portion of intermediate catheter 40 to attain a configuration shown in, e.g., FIG. 2B or 2C, via the shape memory of the material of the distal portion of intermediate catheter 40.

Additionally, system 30 may include one or more balloons for adjusting blood flow characteristics of the vasculature of a subject. For example, a first balloon (not shown) may be positioned along an exterior surface of intermediate catheter 40 and/or within the lumen 38 of guide catheter 32. Such a balloon may be arranged so as to secure a portion of intermediate catheter 40 relative to guide catheter 32. For example, such a balloon (e.g., balloon 28 as shown in FIG. 2D) may be an eccentrically mounted balloon so as to push intermediate catheter 40 toward an inner wall of guide catheter 32 to prevent inadvertent relative movement therebetween. For example, upon establishing the desired trajectory of intermediate catheter 40, such a balloon may be inflated or expanded so as to maintain the desired trajectory throughout the duration of a procedure. Any such balloon positioned within lumen 38 between intermediate catheter 40 and an inner wall of guide catheter 32 may optionally be a perfusion balloon so as to permit antegrade blood flow through the ICA 2 to continue. Alternatively, such a balloon may be a "blocking" balloon such that blood flow is not permitted to pass between intermediate catheter 40 and an inner wall of guide catheter 32 from a location proximal of the balloon to a location distal of the balloon. In such a case, retrograde blood flow may be induced with the addition of a catheter connected to the venous system.

Figure 3:
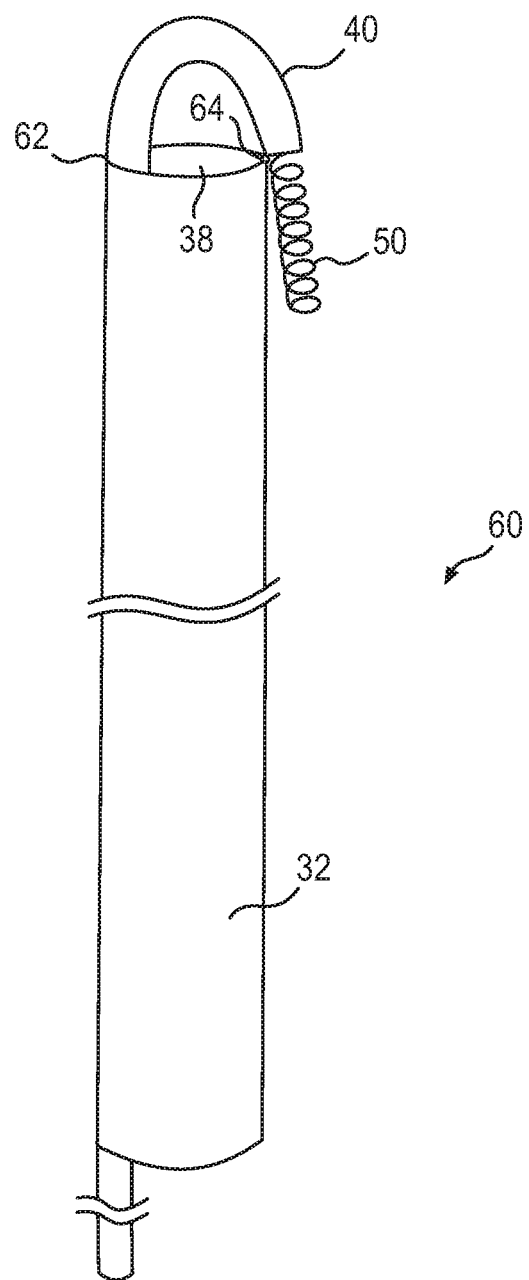
FIG. 3 illustrates a further exemplary system for accessing the OA.

FIG. 3 illustrates an additional system 60 for accessing the OA 4. System 60 is similar to system 30, except that intermediate catheter 40 is fixed so as to be nonmoveable relative to guide catheter 32. For example, intermediate catheter 40 is secured at least at two securing points 62 and 64 relative to guide catheter 32. While only two point contact is illustrated, it is understood that the entire length of intermediate catheter 40 positioned within lumen 38 of guide catheter 32 may be secured to an inner wall of guide catheter 32. For example, intermediate catheter 40 may be glued and/or welded to an inner wall of guide catheter 32.

In further arrangements, any one or both of guide catheter 32 and intermediate catheter 40 may be either pre-shaped or steerable. For example, in some arrangements, intermediate catheter 40 may have a pre-set shape, similar to the shape shown in FIG. 2B, 2C, or 3. In such an arrangement, intermediate catheter 40 may be unsecured to guide catheter 32 (e.g., joint 48, securing points 62, 64 may be omitted). In such an arrangement, the trajectory of the lumen 46 of intermediate catheter 40 may be pre-set such that upon delivery into the vasculature (e.g., via a guide catheter 32) one or more tools 50 may be passed through the lumen 46 of intermediate catheter 40 and into OA 4. Alternatively, rather than a pre-set shape, intermediate catheter 40 may be steerable via any one or more steering wires/cables (not shown).

Figure 4:
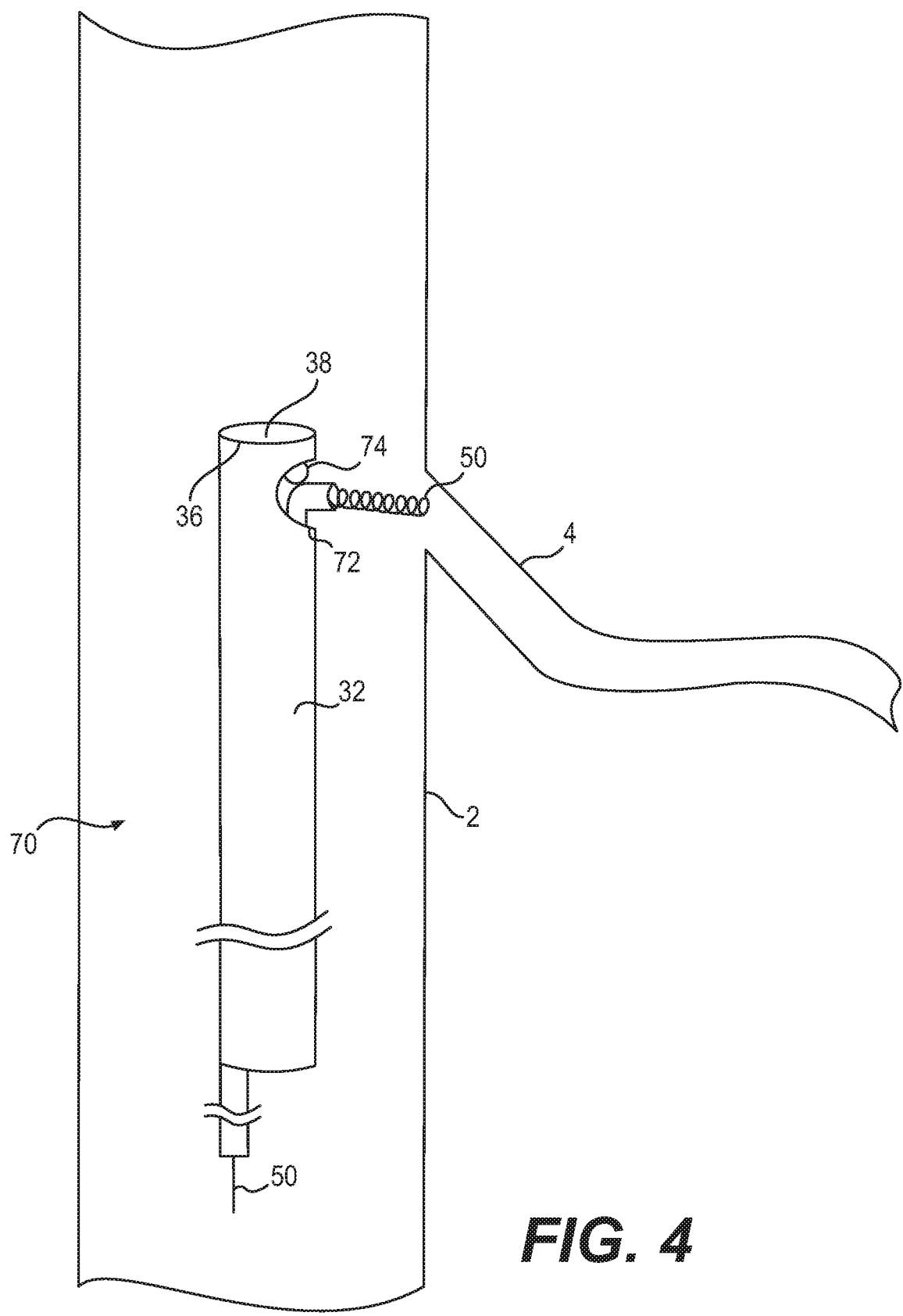
FIG. 4 illustrates another exemplary system for accessing the OA.

FIG. 4 illustrates an additional system 70 for accessing the OA 4. System 70 is similar to systems 30 and 60, except as herein described. For example, guide catheter 32 may further include a side port 72 through which intermediate catheter 40 may be advanced or may be positioned within. Side port 72 may be positioned proximate distal end 36 of guide catheter 32. As shown, in FIG. 4, a protrusion 74 may be positioned at side port 72 so as to guide or direct intermediate catheter 40 towards or through side port 72 along a desired trajectory. In some arrangements, protrusion 74 may be adjustable so as to dynamically modify an angle or trajectory of intermediate catheter 40 extending through side port 72. For example, protrusion 74 may include an adjustable balloon. Upon delivery of an inflation medium (e.g., air, saline, or other gases or liquids), a degree of expansion or inflation of protrusion 74 may be increased so as to further articulate, bend, or re-direct the trajectory of intermediate catheter 40. Protrusion 74 may be coupled to any appropriate inflation medium source in any appropriate manner such as a lumen of guide catheter 32 or any appropriate tubing extending through or alongside guide catheter 32. In some arrangements, one or more portions of intermediate catheter 40 may be secured to an inner wall guide catheter 32. Alternatively, intermediate catheter 40 may be uncoupled from guide catheter 32 except for via protrusion 74 and side port 72. In such a latter arrangement, guide catheter 32 may be advanced into the vasculature first, and then once so positioned, intermediate catheter 40 may be delivered through lumen 38 of guide catheter 32, and through side port 72. Next, the degree of expansion or inflation of protrusion 74 may be adjusted so as to adjust a trajectory of intermediate catheter 40. Alternative embodiments to an inflatable/expandable protrusion 74 include a ramped surface within lumen 38 and leading to side port 72. The ramped surface may be fixed, adjustable, or pivotable to guide intermediate catheter 40 through side port 72.

Figure 5:
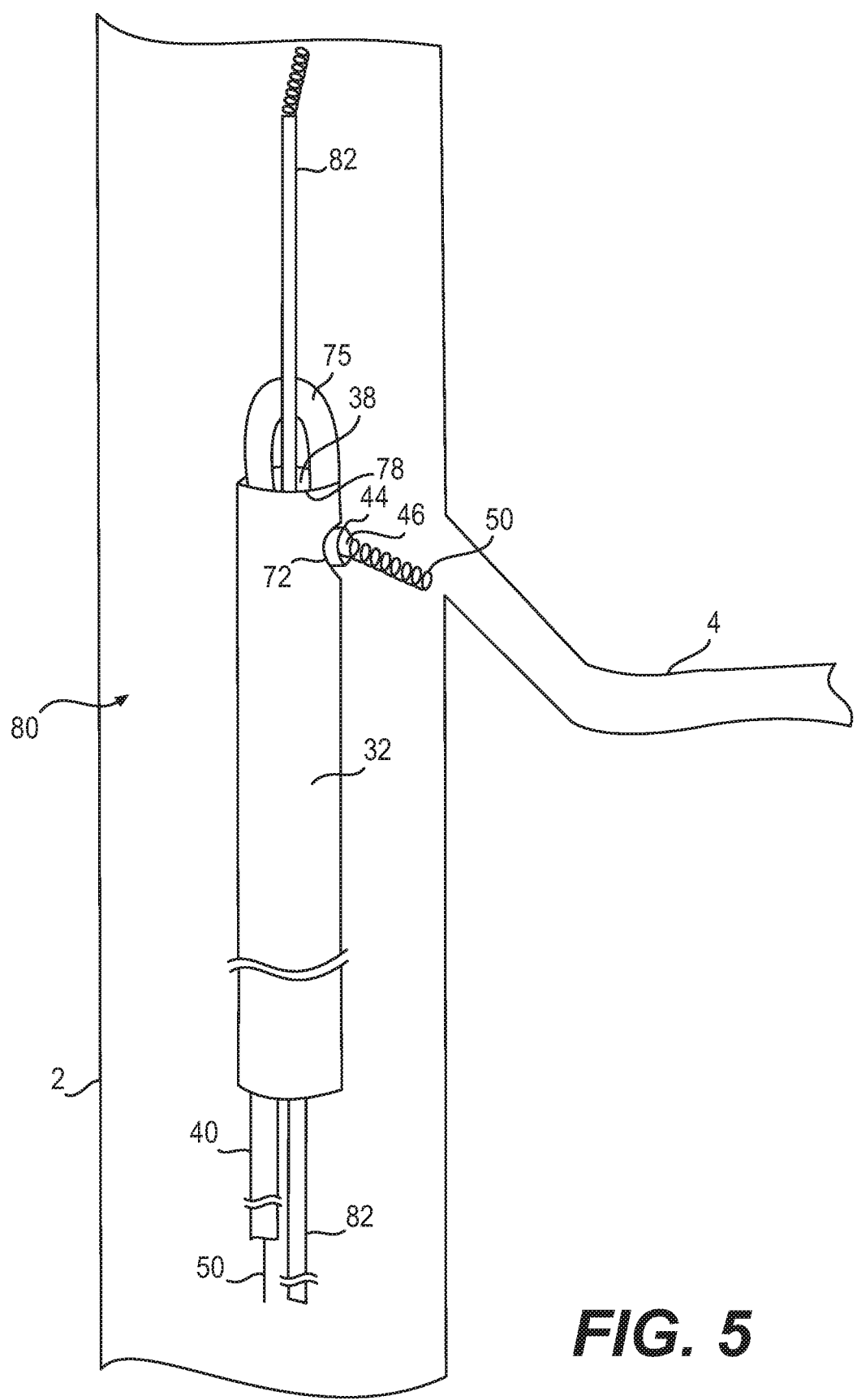
FIG. 5 illustrates a further exemplary system for accessing the OA.
Figure 6:
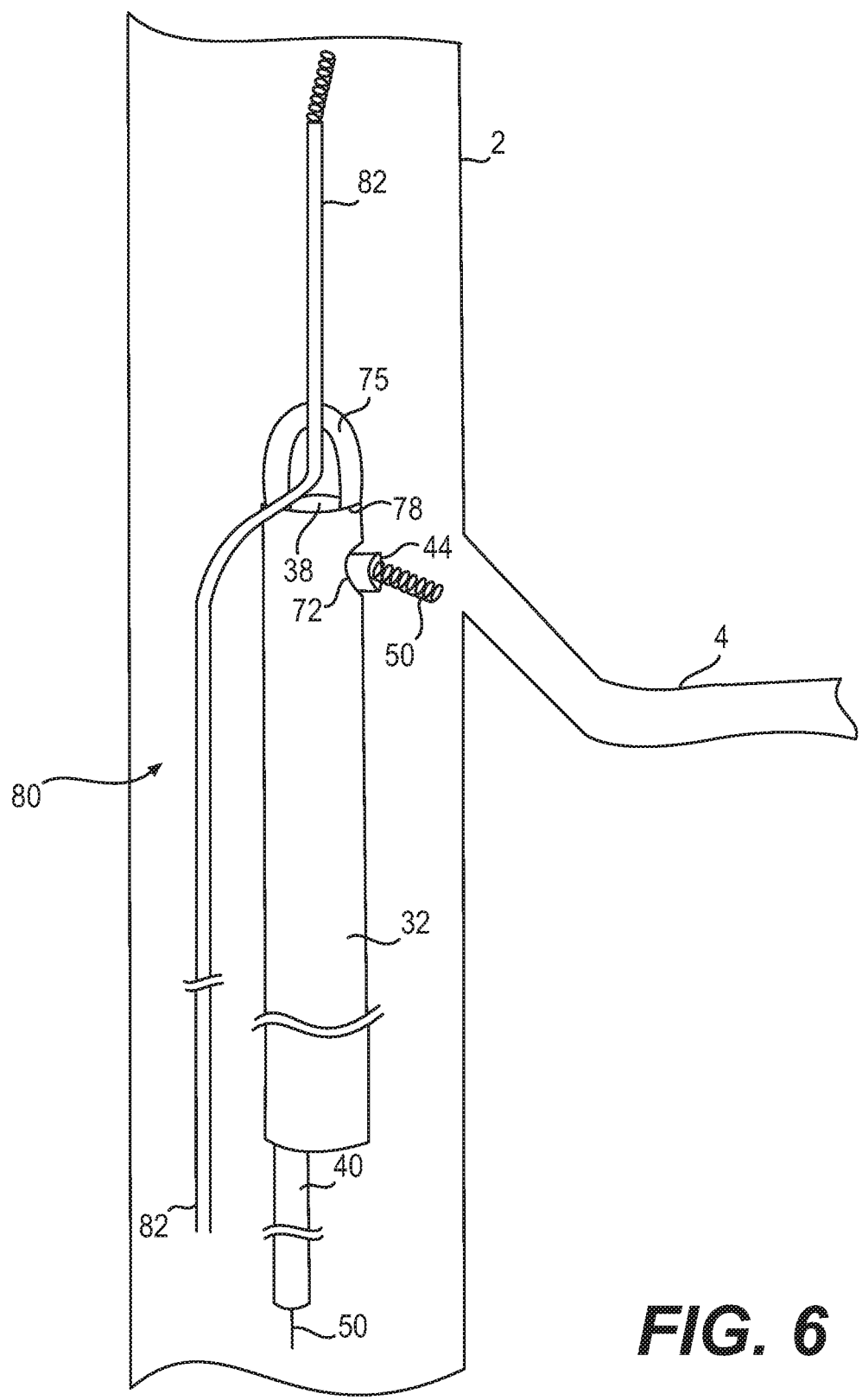
FIG. 6 illustrates an alternative delivery mechanism of the system of FIG. 5.

FIG. 5 illustrates an additional system 80 for accessing the OA 4. System 80 is similar to systems 30, 60, and 70 except as herein described. For example, a portion (e.g., distal region) of intermediate catheter 40 may be bent, curved or otherwise shaped into an s-shape formation such that the portion extends through a distal opening 78 of guide catheter 32, makes an approximately 180° bend in a first direction so as to re-enter lumen 38 of guide catheter 32 through distal opening 78 and form loop 75, and then makes another bend (e.g., an approximately 90° bend) in a second direction, opposite the first direction, such that distal end 44 is positioned within or extends through side port 72. While not shown in FIG. 5, it is understood that a protrusion 74 may be positioned at side port 72 so as to dynamically adjust a trajectory of intermediate catheter 40, as discussed above in connection with FIG. 4. Intermediate catheter 40 may be secured within guide catheter 32 as shown (e.g., via adhesives or welding), or may be moveable relative to guide catheter 32. In such a moveable arrangement, intermediate catheter 40 may be advanced through lumen 38 of guide catheter 32 and steered (e.g., via one or more wires/cables) so as to bend into the s-shape shown in FIG. 5. Once in position, one or more medical devices/tools 50 (e.g., a guidewire such as a platinum coiled guidewire, a balloon, etc.) may be advanced through lumen 46 of intermediate catheter 40 and to a desired location of the anatomy (e.g., within the OA 4). Additionally or alternatively, lumen 46 of intermediate catheter 40 may be coupled to a source of negative pressure (e.g., vacuum, aspiration, suction, etc.) for facilitating retrograde blood flow of OA 4 therethrough, or one or more pharmaceuticals or other fluids may be delivered through lumen 46 of intermediate catheter 40. Due to the small size (e.g., cross-sectional dimension, diameter, etc.) of intermediate catheter 40 relative to the size (e.g., cross-sectional dimension, diameter, etc.) of guide catheter 32, additional devices such as a guidewire 82 may be passed through lumen 38 of guide catheter 32, alongside and without interfering with intermediate catheter 40. Such a guidewire 82 may be use to advance system 80 through the vasculature of a subject. Optionally, once system 80 has been delivered over guidewire 82, guidewire 82 may be removed or withdrawn from guide catheter 32. While shown as extending through lumen 38 of guide catheter 32 in FIG. 5, in a further arrangement, guidewire 82 may inserted within the vasculature, and then system 80 may be advanced alongside guidewire 82. For instance, as shown in FIG. 6, guidewire 82 may be thread or advanced through loop 75 so as to maintain close contact therebetween, without necessitating positioning of guidewire 82 through guide catheter 32. Guide catheter 32 may be delivered to the desired location by advancing guide catheter 32/intermediate catheter 40 over guidewire 82 via loop 75.

Figure 7:
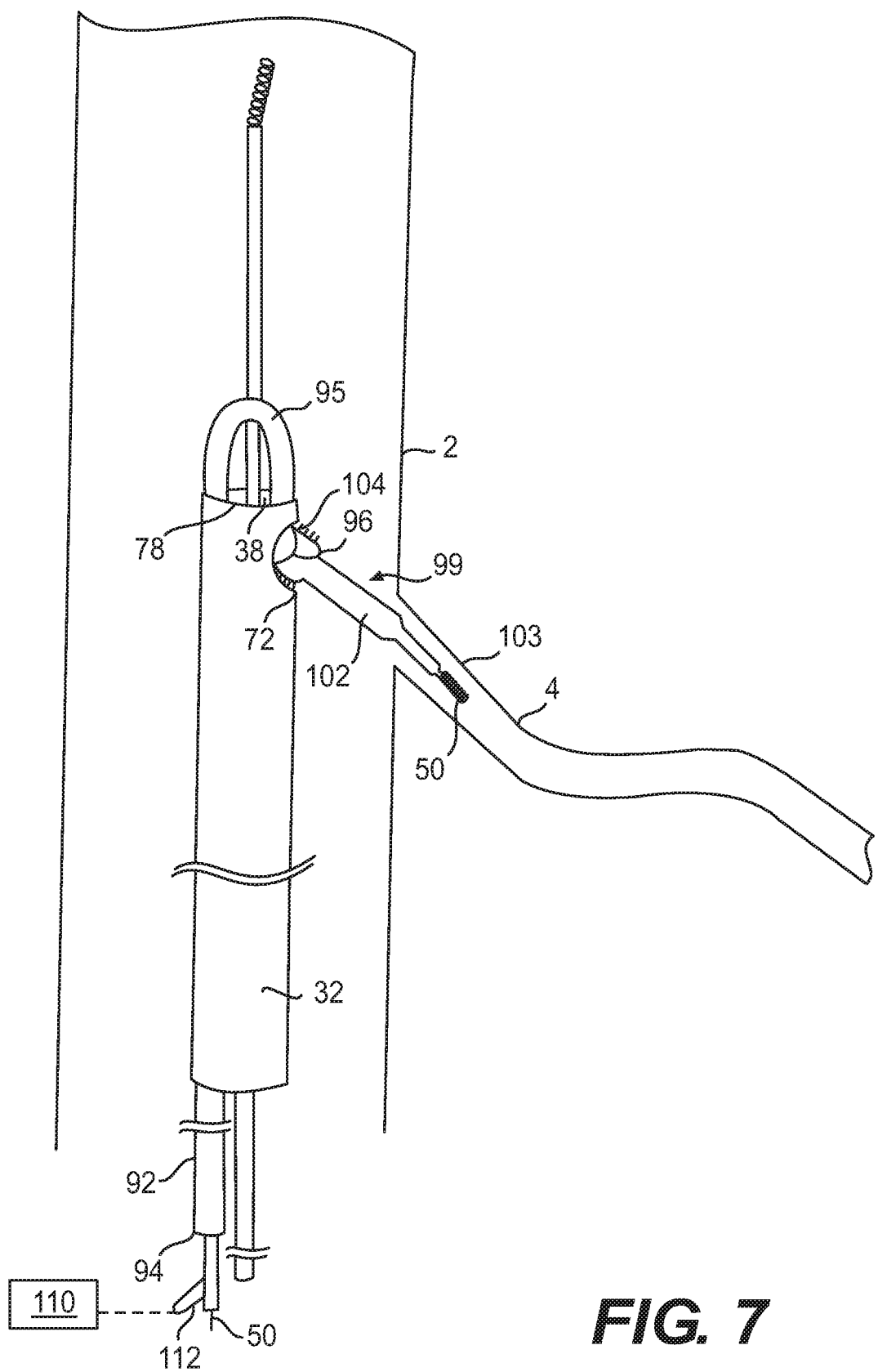
FIG. 7 illustrates an additional exemplary system for accessing the OA.
Figure 8A:
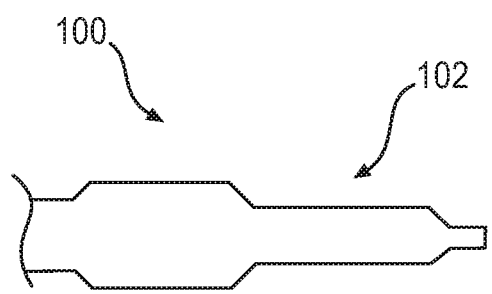
FIGS. 8A and 8B illustrate exemplary cross-sectional shapes of balloons for use with the system of FIG. 7.
Figure 8B:
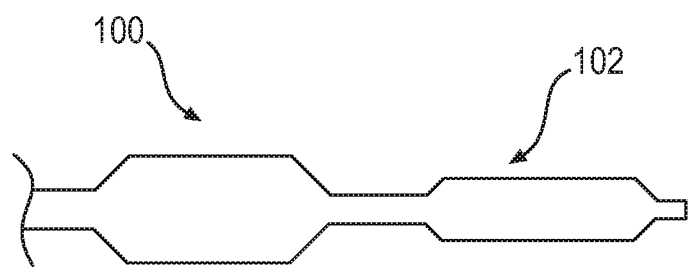

FIG. 7 illustrates an additional system 90 for accessing the OA 4. System 90 is similar to systems 30, 60, 70, and 80 except as herein described. In particular, as shown in FIG. 7, intermediate catheter 40 has been replaced with intermediate catheter 92. Intermediate catheter 92 includes a proximal end 94, a distal end 96, and a lumen 98 extending therebetween. As shown, similar to intermediate catheter 40 of FIGS. 5 and 6, intermediate catheter 92 includes a portion (e.g., distal region) that may be bent, curved or otherwise shaped into an s-shape formation such that the portion extends through a distal opening 78 of guide catheter 32, makes an approximately 180° bend in a first direction so as to re-enter lumen 38 of guide catheter 32 through distal opening 78 and form loop 95, and then makes a bend in a second direction, opposite the first direction, such that distal end 96 extends through side port 72. Additionally, a balloon (e.g., a dual balloon) apparatus 99 may be advanced through intermediate catheter 92 and distally of distal end 96 thereof. A distal region of balloon apparatus 99 may include a plurality of balloons or balloon portions, such as, for example, a first balloon 100 and a second balloon 102. First balloon 100 may be positioned proximal of second balloon 102. Additionally, upon expansion, first balloon 100 and second balloon 102 may be configured to have different cross-sectional dimensions (e.g., diameters). For example, as shown in FIGS. 7, 8A and 8B, first balloon 100 may have a cross-sectional dimension larger than a cross-sectional dimension of second balloon 102. In alternative arrangements, the first balloon 100 may have a cross-sectional dimension smaller than a cross-sectional dimension of second balloon 102. The cross-sectional dimension (e.g., diameter) of first balloon 100 may be sized or selected so as to contact, grip, or otherwise secure first balloon 100 within intermediate catheter 92 and/or within side port 72 so as to retain balloon apparatus 99 relative to guide catheter 32 and/or intermediate catheter 92 so as to avoid second balloon 102 from backing out of OA 4, as will be described in further detail below. First balloon 100 may include texture or other surface features 104 to facilitate secure connection with distal end 96 of intermediate catheter 92.

Second balloon 102 may be positioned distally of first balloon 100 and may have a cross-sectional dimension (e.g., diameter) configured to dilate OA 4. Such dilation may be used to complete an angioplasty or other medical procedure within OA 4, or so that second balloon 102 provides an anchor within OA 4 for the insertion of additional tools or devices. During inflation of second balloon 102 within OA 4, second balloon 102 may be prevented from backing out, "watermeloning," or otherwise escaping out of OA 4 due to the first balloon 100. That is, following expansion of first balloon 100 so as to secure or anchor first balloon 100 relative to intermediate catheter 92, increased leverage or stability may be imparted to balloon apparatus 99 such that inflation of second balloon 102 may cause dilation of OA 4. In addition, one or more medical devices/tools 50 (e.g., a guidewire such as a platinum coiled guidewire, a balloon, a cutting device, a stent, etc.) may be advanced through lumen 103 of balloon apparatus 99 and to a desired location of the anatomy (e.g., within the OA 4). Additionally or alternatively, lumen 93 of balloon apparatus 99 may be coupled to a source of negative pressure (e.g., vacuum, aspiration, suction, etc.) for facilitating retrograde blood flow of OA 4 therethrough, or one or more pharmaceuticals or other fluids may be delivered through lumen 93 of balloon apparatus 99. Each of first balloon 100 and second balloon 102 may be fluidly coupled to a source 110 of inflation fluid (e.g., air, saline, or other gasses or liquids) via a manifold 112. Upon actuation of one or more valves or regulators (not shown), inflation fluid may be delivered via one or more lumens of intermediate catheter 92, and/or lumen 103 of balloon apparatus 99 to first balloon 100 and/or second balloon 102. In some arrangements, first balloon 100 and second balloon 102 are individually inflatable through any appropriate valve/inflation lumen structures. Alternatively, in some arrangements, first balloon 100 and second balloon 102 are simultaneously inflatable through any appropriate valve/inflation lumen structures. It is understood, that manifold 112 and the valve/inflation lumen structures may additionally be used so as to deflate or evacuate first balloon 100 and second balloon 102, as needed.

In any of systems 30, 60, 70, 80, and 90, a trajectory of intermediate catheter 40, 92 may be altered to facilitate precise and quick delivery of one or more medical devices/tool 50, delivery of one or more pharmaceuticals or other fluids or aspiration, and/or receipt of retrograde blood flow of the OA 4 toward ICA 2. The devices and methods described herein enable dynamic adjustment of the trajectory of intermediate catheter 40, 92, and provide a system for delivering medical tools/devices sized for insertion within the OA 4 (e.g., medical devices/tools 50 having a cross-sectional dimension between about 0.2 mm and about 1.8 mm, or generally about 1.0 mm). Additionally, any of guide catheters 32, intermediate catheters 40, 92, and/or guidewires 82 may include one or more portions comprised of radiopaque materials to facilitate visibility via one or more imaging modalities (e.g., X-ray, etc.). Additionally, any of guide catheters 32, intermediate catheters 40, 92, and/or guidewires 82 may include one or more portions comprised of a lubricious material or coated with a lubricious coating so as to reduce friction between various components of any of systems 30, 60, 70, 80, and 90. Additionally, second balloon 102 may be a drug eluting balloon so as to deliver one or more pharmaceuticals to OA 4, if so desired.

While principles of the present disclosure are described herein with reference to illustrative examples for particular applications, it should be understood that the disclosure is not limited thereto. Those having ordinary skill in the art and access to the teachings provided herein will recognize additional modifications, applications, embodiments, and substitution of equivalents all fall within the scope of the features described herein. Accordingly, the claimed features are not to be considered as limited by the foregoing description.

We claim:

1. A method for treating an eye disorder, comprising:
accessing an ophthalmic artery (OA) of a subject through an access vasculature site of the subject via a first device;
positioning a second device within at least a lumen of the OA; and
treating the eye disorder by increasing a size of a first portion of the second device to a first diameter, and increasing a size of a second portion of the second device within the lumen of the OA of the subject to a second diameter, wherein the first diameter is greater than the second diameter.

2. The method of claim 1, wherein increasing the size of the first portion of the second device includes inflating a first balloon positioned in an internal carotid artery (ICA) of the subject, and wherein increasing the size of the second portion of the second device includes inflating a second balloon positioned within the lumen of the OA, thereby dilating the OA.

3. The method of claim 2, wherein the first balloon and the second balloon are individually inflatable.

4. The method of claim 2, wherein the first balloon and the second balloon are simultaneously inflatable.

5. The method of claim 1, further comprising delivering, through the first device or the second device positioned within the lumen of the OA, one or more pharmaceuticals or other fluids to the OA.

6. The method of claim 1, further comprising advancing a third device through an internal carotid artery (ICA) of the subject, and aligning a side port of the third device with a junction between the ICA and the OA, wherein positioning the second device includes advancing the second device through a lumen of the third device, to extend through the side port of the third device into the lumen of the OA.

7. The method of claim 6, wherein positioning the second device includes advancing the first device through the lumen of the third device to extend through the side port of the third device, and advancing the second device through a lumen of the first device.

8. The method of claim 1, further including anchoring the second device relative to the first device to inhibit backing out of the second device from the OA.

9. A method for treating an eye disorder, comprising:
accessing an internal carotid artery (ICA) of a subject through an access vasculature site of the subject via a first device;
advancing a second device through a lumen and a port of the first device;
positioning at least a distal portion of the second device within a lumen of an ophthalmic artery (OA) of the subject; and
treating the eye disorder by increasing a size of a first portion of the second device, to a first diameter, and increasing a size of the second portion of the second device, the second portion of the second device being distal of the first portion of the second device and located within the lumen of the OA, to a second diameter, wherein the first diameter is greater than the second diameter.

10. The method of claim 9, wherein the first portion of the second device is a first balloon and the second portion of the second device is a second balloon, and wherein increasing the size of the first portion of the second device includes dilating the first balloon, and increasing the size of the second portion of the second device includes dilating the second balloon located within the lumen of the OA.

11. The method of claim 9, further including orienting the port of the second device toward a junction between the OA and the ICA.

12. The method of claim 9, further including anchoring the second device relative to the first device to inhibit backing out of the second device from the OA.

13. The method of claim 9, further comprising delivering, through the second device, at least partially positioned within lumen of the OA, one or more pharmaceuticals or other fluids to the OA.

14. The method of claim 9, further comprising:
advancing a third device through the first device within the ICA; and
aligning a port of the third device with a junction between the ICA and the OA, wherein positioning at least the distal portion of the second device includes advancing at least the second portion of the second device through a lumen of the third device, to extend through the port of the third device into the lumen of the OA.

15. The method of claim 14, wherein positioning at least the distal portion of the second device includes advancing the third device through the lumen of the first device to extend through the port of the first device, and advancing at least the second portion of the second device through a lumen of the third device and into the lumen of the OA.

16. The method of claim 9, wherein the second device is a dual balloon device, including a first balloon as the first portion, and a second balloon as the second portion that is distal of the first balloon.

17. A method for treating an eye disorder, comprising:
accessing an internal carotid artery (ICA) of a subject through an access vasculature site of the subject via a first device;
advancing a second device through a lumen and a side port of the first device, the second device extending through a distal opening of the first device, making an approximately 180° bend in a first direction so as to reenter the lumen of the first device through the distal opening and form a loop, and bending in a second direction, different from the first direction, so as to extend through the side port of the first device;
advancing a third device through a lumen of the second device, and positioning at least a portion of the third device within a lumen of an ophthalmic artery (OA) of the subject; and
treating the eye disorder by increasing a size of a distal portion of the third device.

18. The method of claim 17, wherein increasing the size of the distal portion of the third device includes inflating a distal balloon, positioned in the lumen of the OA.

19. The method of claim 18, further comprising inflating a proximal balloon, located within one of the lumen and the side port of the first device.

20. The method of claim 19, wherein the distal balloon and the proximal balloon are simultaneously inflatable.

* * * * *